(12) United States Patent
Silver et al.

(10) Patent No.: US 10,702,306 B2
(45) Date of Patent: Jul. 7, 2020

(54) SYSTEM AND METHOD FOR CONTROLLING THE PERFORMANCE OF A PNEUMATICALLY SEALED TROCAR

(71) Applicant: Conmed Corporation, Utica, NY (US)

(72) Inventors: Mikiya Silver, New Haven, CT (US); Michael J. Kane, Clinton, CT (US)

(73) Assignee: Conmed Corporation, Utica, NY (US)

( * ) Notice: Subject to any disclaimer, the term of this patent is extended or adjusted under 35 U.S.C. 154(b) by 278 days.

(21) Appl. No.: 15/817,897

(22) Filed: Nov. 20, 2017

(65) Prior Publication Data

US 2019/0150981 A1    May 23, 2019

(51) Int. Cl.
  *A61B 17/34*    (2006.01)
  *A61M 13/00*    (2006.01)
  *A61B 17/00*    (2006.01)

(52) U.S. Cl.
  CPC ...... *A61B 17/3474* (2013.01); *A61B 17/3423* (2013.01); *A61M 13/006* (2014.02); *A61B 2017/00172* (2013.01); *A61B 2017/00544* (2013.01); *A61B 2017/00734* (2013.01); *A61B 2017/3419* (2013.01); *A61M 2205/3334* (2013.01); *A61M 2205/3344* (2013.01); *A61M 2205/50* (2013.01)

(58) Field of Classification Search
  CPC .............. A61M 13/003; A61M 13/006; A61B 17/3474; A61B 17/3423
  See application file for complete search history.

(56) References Cited

U.S. PATENT DOCUMENTS

| | | | |
|---|---|---|---|
| 5,586,974 A * | 12/1996 | Martinez | A61M 13/003 251/314 |
| 6,695,823 B1 * | 2/2004 | Lina | A61F 13/0203 602/43 |
| 7,854,724 B2 | 12/2010 | Stearns et al. | |
| 8,715,219 B2 | 5/2014 | Stearns et al. | |
| 8,795,223 B2 | 8/2014 | Stearns et al. | |
| 8,961,451 B2 | 2/2015 | Stearns et al. | |

(Continued)

FOREIGN PATENT DOCUMENTS

JP       2001506509 A     5/2001

OTHER PUBLICATIONS

International Search Report issued in corresponding PCT Patent Application No. PCT/US2018/056704, dated Mar. 29, 2019.

(Continued)

*Primary Examiner* — Laura A Bouchelle
(74) *Attorney, Agent, or Firm* — Locke Lord LLP; Scott D. Wofsy (57) ABSTRACT

A system and method is disclosed for controlling the performance of a pneumatically sealed trocar, wherein the system includes a controller for delivering variable DC voltage to a DC motor, a DC motor operatively connected to the controller for driving a pump operatively connected to a pneumatically sealed trocar, a pump driven by the DC motor for circulating pressurized gas through the pneumatically sealed trocar, and a sensor for sensing pressure and flow parameters between the pump and the pneumatically sealed trocar to provide a feedback control signal to the controller so that the controller can vary the voltage delivered to the DC motor to affect the output pressure and flow of the pump during a laparoscopic surgical procedure.

7 Claims, 5 Drawing Sheets

(56) References Cited

U.S. PATENT DOCUMENTS

| | | |
|---|---|---|
| 9,295,490 B2 | 3/2016 | Stearns et al. |
| 2012/0041288 A1 | 2/2012 | Essalik et al. |
| 2013/0303852 A1* | 11/2013 | Hiraga .................. A61B 1/015 |
| | | 600/118 |
| 2015/0290387 A1* | 10/2015 | Mollstam ............ A61M 3/0283 |
| | | 604/24 |
| 2017/0000959 A1* | 1/2017 | Mantell .............. A61B 17/3474 |
| 2017/0157324 A1 | 6/2017 | Yodfat et al. |
| 2017/0215912 A1 | 8/2017 | Truckai |

OTHER PUBLICATIONS

Written Opinion of the international searching authority issued in corresponding PCT Patent Application No. PCT/US2018/056704, dated Mar. 29, 2019.

* cited by examiner

SYSTEM AND METHOD FOR CONTROLLING THE PERFORMANCE OF A PNEUMATICALLY SEALED TROCAR

BACKGROUND OF THE INVENTION

1. Field of the Invention

The subject disclosure relates to gas delivery systems for use with surgical access devices, and more particularly, to a system and method for controlling the performance of a pneumatically sealed trocar used in endoscopic or laparoscopic surgical procedures.

2. Description of Related Art

Pneumatically sealed trocars such as those disclosed for example in commonly assigned U.S. Pat. Nos. 7,854,724 and 8,795,223 can be operated via an electro-mechanical control system. Such control systems are disclosed for example in commonly assigned U.S. Pat. Nos. 8,715,219, 8,961,451, and 9,295,490. These systems function to create and maintain a pneumatic or gaseous seal within the trocar that creates a defined pressure gradient for minimally-invasive laparoscopic or endoscopic surgeries. Those skilled in the art of those surgeries (such as a surgeon or nurse) may choose to pressurize (insufflate) a surgical cavity to a particular pressure in order to better enable visualization of the anatomy and other benefits of insufflation. Each of the above referenced commonly assigned patents are hereby incorporated by reference in their entireties.

When operating a pneumatically sealed trocar via an electro-mechanical control system, it can be advantageous to modulate pneumatic power supplied to the trocar in order to vary its performance behavior and/or characteristics. Design and manufacturing differences may allow for variations in the pneumatic power required to seal a pneumatically-sealed trocar. This can be affected by design, manufacturing variability, area of the seal required (i.e., a 5 mm trocar versus a 12 mm trocar), efficiency, resistance, and other factors.

The pneumatic power required to seal a pneumatically-sealed trocar is also dependent on the magnitude of the pressure gradient maintained by the pneumatic seal. For example, a surgical team might choose to insufflate a patient to 15 mmHg, requiring the pneumatic seal in a pneumatically-sealed trocar to maintain a gradient between 15 mmHg and ambient pressure (0 mmHg). The power required to maintain this seal (gradient) is larger than the power required to maintain a gradient between 10 mmHg and 0 mmHg, for example.

Furthermore, during normal operation of a pneumatically-sealed trocar, regular disturbances or perturbations can be expected. These can include, but are not limited to physiology-driven changes to the insufflated cavity (e.g., from breathing or muscle movement), exterior forces applied to the insufflated cavity (from a surgeon or surgical instrument pressing against the cavity), or from passage of instruments or specimens through the seal of the pneumatically-sealed trocar.

Therefore, an electro-mechanical control system operating a pneumatically sealed trocar should be able to modulate power supplied to that trocar in real-time to respond to those disturbances and maintain the seal and pressure gradient as specified. The control system disclosed in U.S. Pat. No. 8,715,219 includes an electro-mechanical control valve that modulates pneumatic power supplied to the trocar. In that system, a pump (typically driven by AC or alternating current) oversupplies the pneumatic circuit with pressure and gas flow. The pneumatic power that is supplied to the pneumatically-sealed trocar is modulated by an embedded control system that adjusts the electro-mechanical valve.

Those skilled in the art of systems or pneumatics engineering will appreciate the design of the pneumatic circuitry, and the role this valve plays as an "H" or "by-pass" valve. The AC driven pump in that system embodiment supplies a constant power output, and the position of the electro-mechanical valve controls the percentage of that power that reaches the pneumatically-sealed trocar and the percentage that is recycled back to the vacuum intake of the pump.

Those skilled in the art will readily appreciate that there are advantages to using a DC-based control system over an AC-based system for the pneumatic control of a pneumatically-sealed trocar, including improved energy efficiency. Therefore, it would be beneficial to provide a control system that is configured to modulate the pneumatic power supplied to a pneumatically-sealed trocar in real-time via a DC driven pump, rather than an AC driven pump.

SUMMARY OF THE DISCLOSURE

The subject invention is directed to a new and useful system for controlling the performance range of a pneumatically sealed trocar during an endoscopic or laparoscopic surgical procedure. In an embodiment of the subject invention, the system includes a controller for delivering variable DC voltage to a DC motor, a DC motor operatively connected to the controller for driving a pump operatively connected to a pneumatically sealed trocar, a pump driven by the DC motor for circulating pressurized gas through the pneumatically sealed trocar, and a sensor for sensing pressure and/or flow parameters between the pump and the trocar to provide a feedback control signal to the controller so that the controller can vary the voltage delivered to the DC motor to affect the output pressure and flow of the pump. Preferably the system further includes an AC input voltage source and an AC-DC converter for supplying DC voltage to the controller.

In another embodiment of the subject invention, the system includes a controller for delivering variable DC voltage to at least one DC motor, at least one DC motor operatively connected to the controller for driving at least one pump operatively connected to a pneumatically sealed trocar, at least one pump driven by the DC motor for circulating pressurized gas through the pneumatically sealed trocar, and at least one sensor for sensing pressure and/or flow parameters between the at least one pump and the pneumatically sealed trocar to provide at least one feedback control signal to the controller so that the controller can vary the voltage delivered to the at least one DC motor to affect the output pressure and flow of the at least one pump during an endoscopic or laparoscopic surgical procedure.

In an embodiment of the invention, the at least one sensor includes a first sensor for sensing positive pressure and flow parameters between the at least one pump and an inlet port of the pneumatically sealed trocar to provide a first feedback control signal to the controller and a second sensor for sensing negative pressure and/or flow parameters between the at least one pump and an outlet port of the pneumatically sealed trocar to provide a second feedback control signal to the controller.

In another embodiment, the at least one DC motor includes at least a first DC motor for driving at least one positive pressure pump connected to the pneumatically sealed trocar and at least a second DC motor for driving at least one negative pressure pump connected to the pneumatically sealed trocar. In this embodiment, the at least one sensor includes a first sensor for sensing positive pressure and/or flow parameters between the positive pressure pump and an inlet port of the pneumatically sealed trocar to provide a first feedback control signal to the controller and a second sensor for sensing negative pressure and/or flow parameters between the negative pressure pump and the outlet port of the pneumatically sealed trocar to provide a second feedback control signal to the controller.

In another embodiment of the invention, the at least one pump includes at least first and second pumps that are arranged in parallel and are driven by the at least one DC motor. It is envisioned that controller could be adapted and configured to control the first and second pumps at the same or different output levels to meet different system requirements.

In yet another embodiment of the invention, the at least one DC motor and the AC-to-DC converter are replaced by at least one brushless stepper motor, at least one motor driver, and a pulse generator, which function together as a type of DC controller, though technically the performance output is not controlled solely by modulating supplied DC voltage. The mechanical and pneumatic outputs of the components in this embodiment are controlled precisely by electrical signal modulation, as in the DC motor embodiments described previously. However, in this case rather than modulating DC voltage, electrical pulses controlled from a pulse generator are varied and supplied to a motor driver that drives a brushless stepper motor.

More particularly, electrical pulses of varying strength and length may be used to control precise rotation of the stepper motor by movements of a magnetic field generated by magnets in the motor. This will allow for precision control of motor behavior as well as accurate and repeatable start/stop behavior.

The subject invention is also directed to a new and unique method for controlling the performance range of a pneumatically sealed trocar. The method includes the steps of providing a pump for circulating pressurized gas through a pneumatically sealed trocar, driving the pump by way of a DC motor, and controlling the voltage delivered to the DC motor based upon sensed parameters of gas flowing between the pump and the pneumatically sealed trocar to affect the output pressure and flow of the pump during a laparoscopic surgical procedure. The method also preferably includes the step of sensing pressure and/or flow parameters of the gas flowing between the pump and the pneumatically sealed trocar.

These and other features of the control system and method of the subject invention and the way in which it is employed will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art will readily understand how to use the control system and method of the subject invention without undue experimentation, preferred embodiments thereof will be described in detail herein below with reference to the figures wherein.

DETAILED DESCRIPTION OF THE PREFERRED EMBODIMENTS

Figure 1:
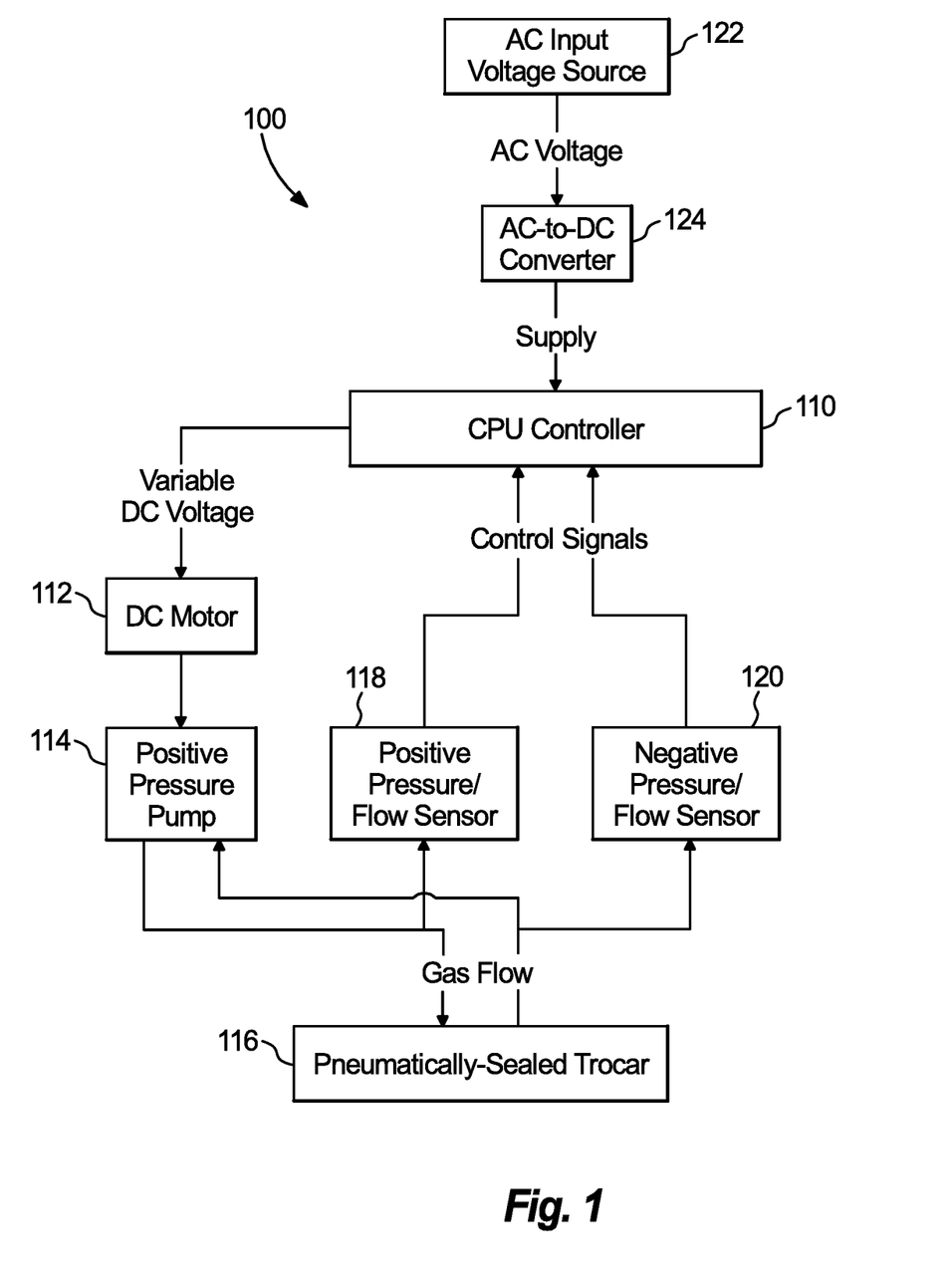
FIG. 1 is a schematic flow diagram illustrating a preferred embodiment of the control system of the subject invention that includes a positive pressure pump driven by a variable voltage controlled DC motor.

Referring to the drawings wherein like reference numerals identify similar features or aspects of the embodiments of the subject invention, there is illustrated in FIG. 1 a system for controlling the performance range of a pneumatically sealed trocar during an endoscopic or laparoscopic surgical procedure, which is constructed in accordance with a preferred embodiment of the subject invention and designated generally by reference numeral 100.

Referring to FIG. 1, the system 100 includes a controller 110 for delivering variable DC voltage to a DC motor 112. The DC motor 112 is operatively connected to the controller 110 for driving a positive pressure pump 114 that is operatively connected to a pneumatically sealed trocar 116. The pump 114 is driven by the DC motor 112 to circulate pressurized gas through the pneumatically sealed trocar 116. A first sensor 118 is provided for sensing positive pressure and/or flow parameters between the pump 114 and an inlet port of the pneumatically sealed trocar 116 to provide a first feedback control signal to the controller 110.

A second sensor 120 is provided for sensing negative pressure and/or flow parameters between the pump 114 and an outlet port of the pneumatically sealed trocar 116 to provide a second feedback control signal to the controller 110. The first and second feedback control signals enable the controller 110 to vary the voltage delivered to the DC motor 112 to affect the output pressure and/or flow of the pump 114. The system 100 further includes an AC input voltage source 122 and an AC-DC converter 124 for supplying DC voltage to the controller 110.

Figure 2:
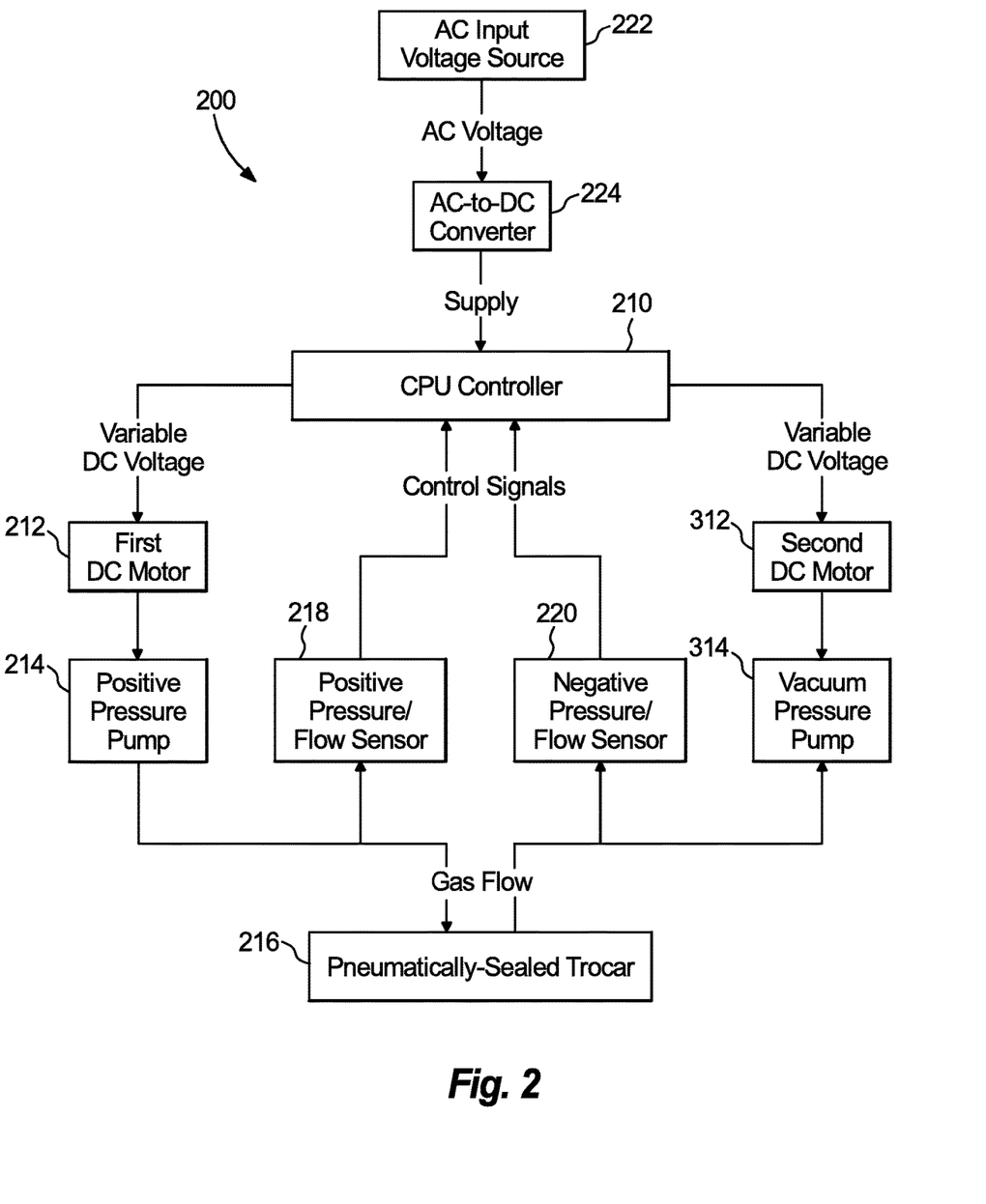
FIG. 2 is a schematic flow diagram illustrating another preferred embodiment of the control system of the subject invention that includes a positive pressure pump driven by a first variable voltage controlled DC motor and a negative pressure pump driven by a second variable voltage controlled DC motor.

Referring to FIG. 2, there is illustrated another embodiment of the control system of the subject invention, which is designated generally by reference numeral 200. System 200 differs from system 100 in that it includes a first DC motor 212 for driving a positive pressure pump 214 connected to a pneumatically sealed trocar 216 and a second DC motor 312 for driving a negative pressure pump 314 connected to the pneumatically sealed trocar 216. The system 200 further includes a first sensor 218 for sensing positive pressure and/or flow parameters between the positive pressure pump 214 and an inlet port of the pneumatically sealed trocar 216 to provide a first feedback control signal to a controller 210 and a second sensor 220 for sensing negative pressure and/or return flow parameters between the negative pressure pump 314 and the outlet port of the pneumatically sealed trocar 216 to provide a second feedback control signal to the controller 210. As in the previous embodiment of FIG. 1, the system 200 further includes an AC input voltage source 222 and an AC-DC converter 224 for supplying DC voltage to the controller 210.

Figure 3:
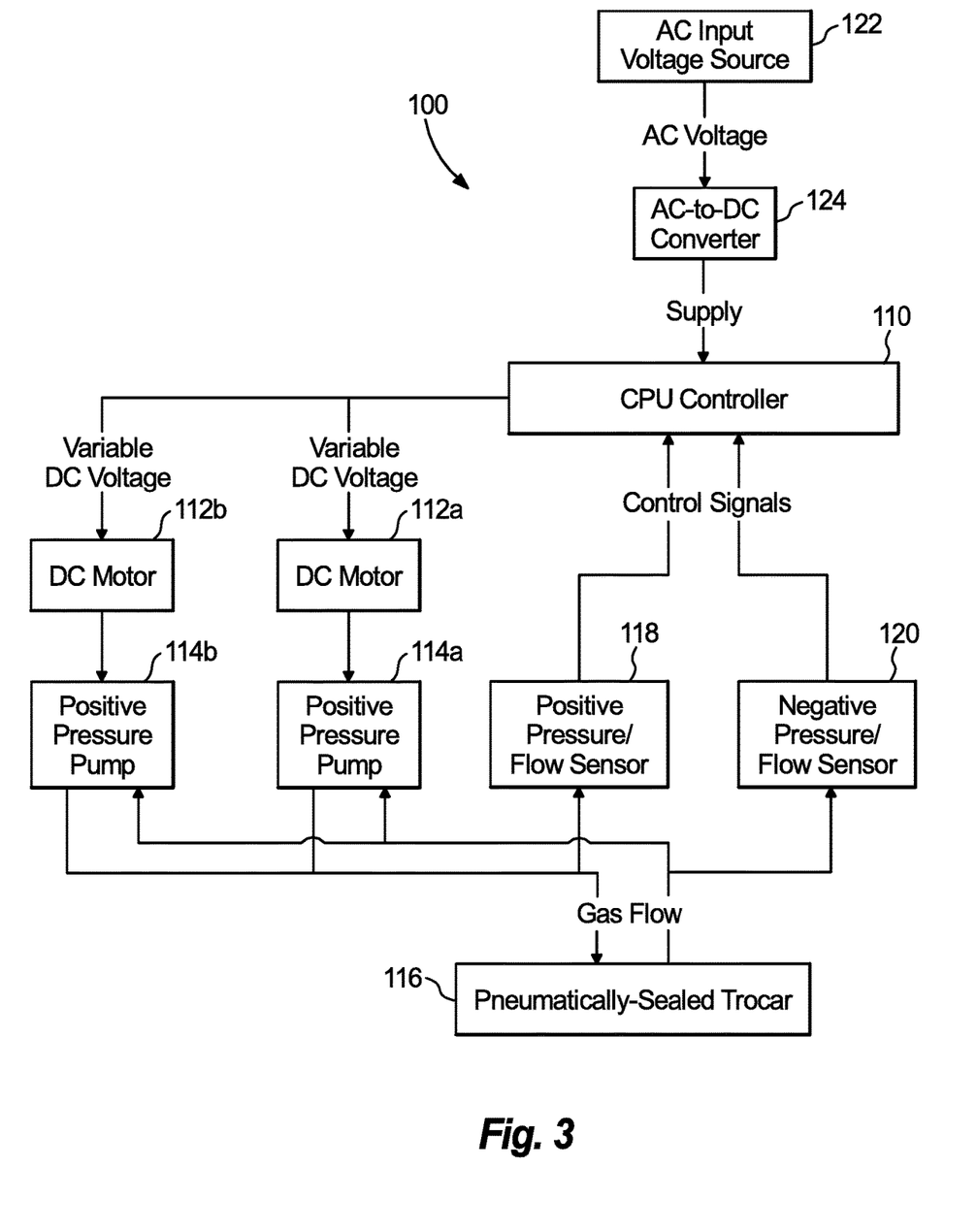
FIG. 3 is a schematic flow diagram illustrating another preferred embodiment of the control system of the subject invention that includes two positive pressure pumps pneumatically plumbed in parallel and driven by two variable voltages that control parallel DC motors.

Referring now to FIG. 3, there is illustrated a modified version of the control system 100 shown in FIG. 1. Here, the system 100 includes two positive pressure pumps 114*a* and 114*b*, driven by respective DC motors 112*a* and 112*b*. These pumps and motors are arranged or otherwise stacked in parallel to increase the pneumatic power capabilities of the system 100, and provide additional control options to improve system efficiency. Moreover, by placing two DC driven pumps in parallel, twice the pneumatic output can be supplied. In this instance, the controller or CPU 110 controls the performance output of one or both of the pumps, depending upon the system demands.

For example, if the two pumps 114*a*, 114*b* each have a 50 L/min capacity and they are combined in parallel, and the operating range of the system 100 always requires between 50-100 L/min, the first pump 114*a* could always be controlled to 100% of its output (i.e., 50 L/min), while the output of the second pump 114*b* could be variably controlled to between 0-50 L/min, in order to achieve the system requirement.

Alternatively, both DC driven pumps 114*a*, 114*b* could be controlled to the same output level. For example, to achieve an 80 L/min output, both pumps 114*a*, 114*b* would be controlled to a 40 L/min output. Or, to achieve 80 L/min output, the two pumps 114*a*, 114*b* could be controlled to different levels. For example, pump 114*a* could be controlled to 45 L/min and pump 114*b* could be controlled to 35 L/min.

In each of these alternate embodiments with multiple motors and pumps, a larger DC power supply would be required (e.g., 24V to supply two 12V motors) and the CPU 110 will be responsible for dividing and regulating the voltage supplied between the two motors 112*a*, 112*b* as specified, which in turn, will control the output of their respective pumps 114*a*, 114*b*. While this embodiment of FIG. 3 has been shown and described as having two DC driven positive pressure pumps stacked together in a parallel relationship, it is envisioned that more than two pumps or similar or varying capacity can be arranged in this manner to further increase and diversify the operational capabilities of the control system disclosed herein.

Figure 4:
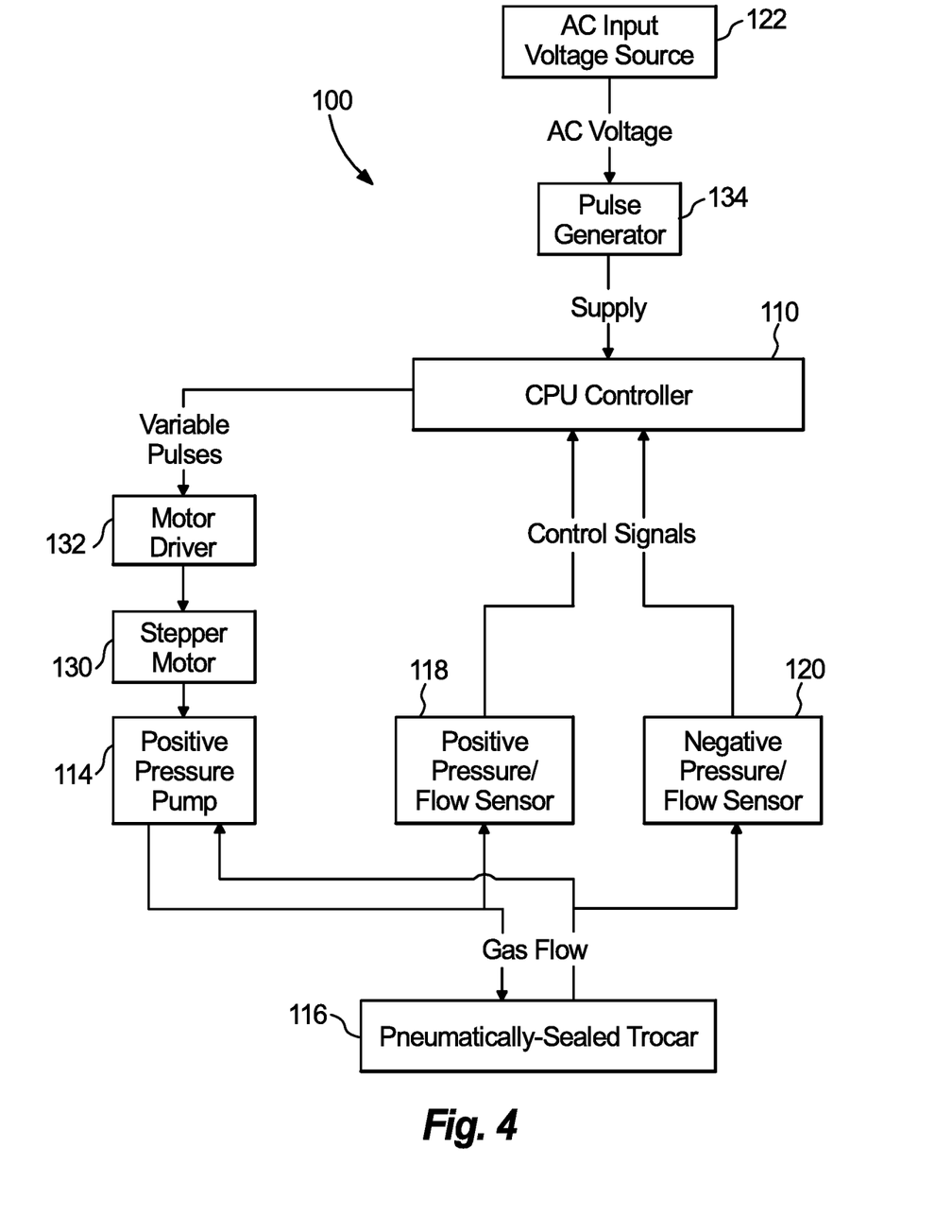
FIG. 4 is a schematic flow diagram illustrating another preferred embodiment of the control system of the subject invention that includes a positive pressure pump driven by a stepper motor controlled by a motor driver which is modulated by variable electrical pulses from a pulse generator.

Referring to FIG. 4, there is illustrated another version of the control system 100 shown in FIG. 1. In this embodiment of the subject invention, the DC motor 112 and the AC-to-DC converter 124 shown in FIG. 1 are replaced by a brushless stepper motor 130, a motor driver 132, and a pulse generator 134. Those skilled in the art might classify this embodiment as a type of DC controller, though technically the performance output is not controlled solely by modulating supplied DC voltage. Nevertheless, those skilled in the art will appreciate the similarities of this embodiment of the invention to other types of DC-controlled systems.

The mechanical and pneumatic outputs of the components in this embodiment are controlled precisely by electrical signal modulation, as in the DC motor embodiments described previously. However, in this case rather than modulating DC voltage, electrical pulses controlled from pulse generator 134 are varied and supplied to motor driver 132 that drives the brushless stepper motor 130. More particularly, electrical pulses of varying strength and length are used to control precise rotation of the stepper motor 130 by precise movements of a magnetic field generated by magnets in the motor. This allows for precision control of motor behavior as well as accurate and repeatable start/stop behavior. Those skilled in the art will appreciate that gear-like geometry of a stepper motor also enables a control system that verifies the number of "steps" of the gear as part of its embedded controls, which may allow for simpler design of the feedback loop to control pneumatic performance of the system by alleviating the need for at least one separate sensor (such as sensor 118 or 120).

Figure 5:
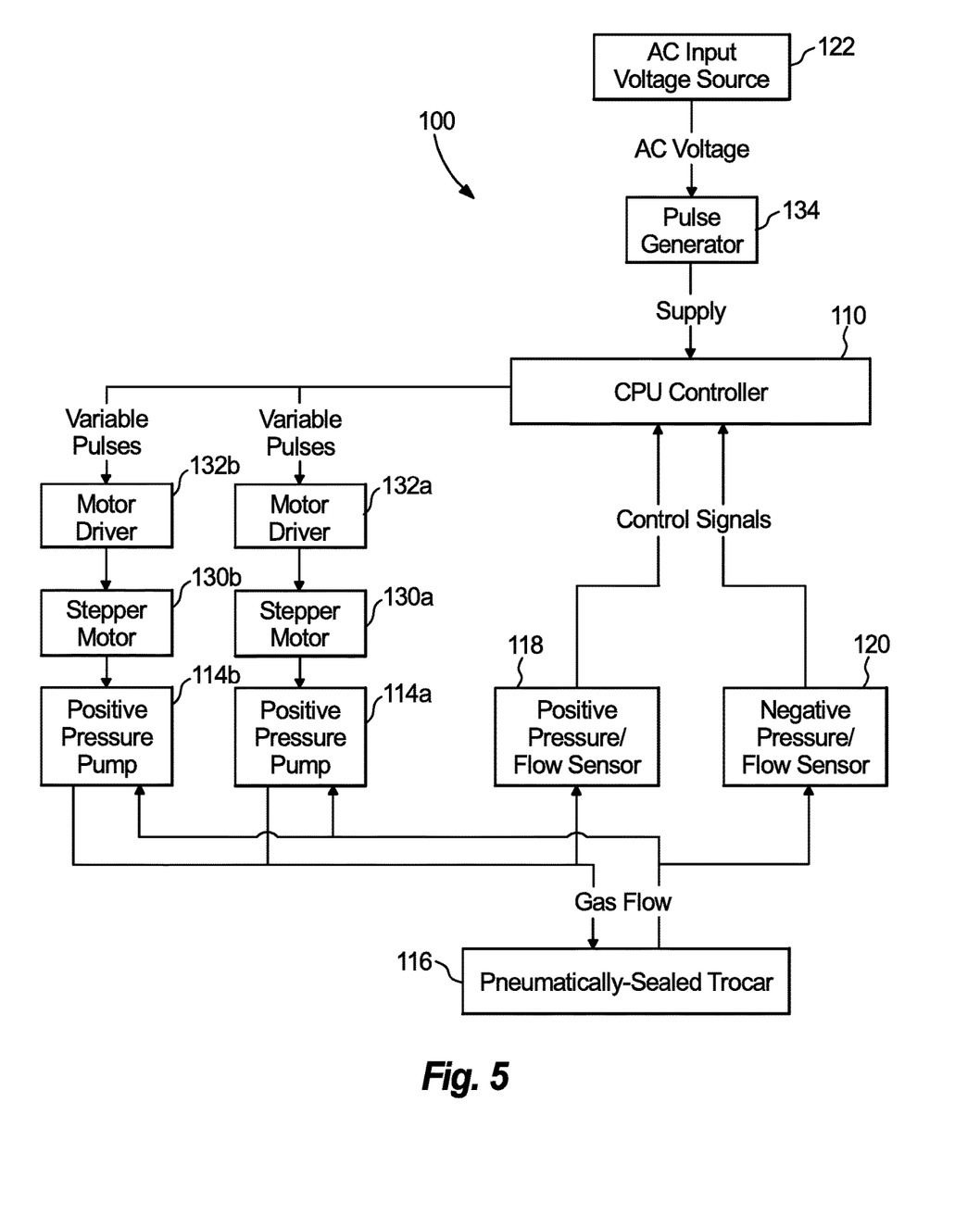
FIG. 5 is a schematic flow diagram illustrating yet another preferred embodiment of the control system of the subject invention that includes two positive pressure pumps driven by respective stepper motors controlled by respective motor drivers which are modulated by variable electrical pulses from a pulse generator.

While the embodiment of FIG. 4 has been shown and described as having one motor driver 132, one stepper motor 130 and one positive pressure pump 114, it is envisioned and well within the subject disclosure, that groupings of these three components (132, 130, 114) can be arranged in a parallel relationship as shown for example in FIG. 5, to further increase and diversify the operational capabilities of the control system 100 disclosed herein. More particularly, as shown in FIG. 5, the controller 110 can be configured to deliver variable pulse signals supplied by pulse generator 134 to a first grouping of components including motor driver 132*a*, stepper motor 130*a* and positive pressure pump 114*a*, as well as a second parallel grouping of components including motor driver 132*b*, stepper motor 130*b* and positive pressure pump 114*b*. It is envisioned that controller 110 would be configures to deliver the same or different strength or duration variable pulses to the parallel sets of components to meet system requirements.

Referring now in general to the various embodiments of the subject invention described herein, those skilled in the art of embedded system controls will know of several methods of supplying, modulating, and controlling a component or system behavior by varying voltage supplied to a DC component like a pump. The required components may include, but are not limited to, a power supply converter or battery, a potentiometer (which varies circuit resistance to control voltage supplied to the DC component), a computer board (e.g., Arduino or the like), a permanent magnet motor, and others.

The power supply converter or battery is used to supply the DC component with direct current (DC) rather than supplying alternating current (AC), which is supplied normally by power outlets and grids. Controlling the voltage supplied to the DC component will vary its performance output. For example, a 12V DC motor will output more power when supplied with 10V than it would when supplied with 6V. This control is frequently achieved via a loop controller in which a sensor measuring performance output (or some related metric) communicates with the computer board, which is programmed with a response. The computer board will trigger a change to the variable power supplied to the motor when the data from the sensor requires such change.

The method and apparatus of the subject invention modulates pneumatic power supplied to a pneumatically-sealed trocar in real-time via control of the pneumatic output of a DC driven pump. In the system 100 of FIG. 1, the control loop is designed around three main components: a CPU control board 110, a motor 112 that drives the pump 114, and a sensor 118. In this preferred embodiment, the system 100 consists of a transformer 124 that converts the AC current from the wall (outlet supply) to DC. Alternatively, you could have a battery that charges from the AC current and directly provides DC power. The available power supply must meet or exceed the rating of the powered component (for example, DC power supply must be 12V to fully power a 12V motor). After being converted, the CPU modulates how much voltage is supplied to the motor 112.

Varying the voltage to the motor 112 will directly affect the pressure and flow output of the pump 114, which is recorded by sensor 118 that loops back to the CPU 110, informing the CPU of the system performance and guiding how to respond to continue control and modulation of the system 100 as required. Alternatively, the CPU 110 could modulate voltage supply to the motor 112 to vary and control vacuum pressure and gas flow using data from the negative pressure sensor 120.

The CPU 110 could control a component like a potentiometer to modulate DC voltage supplied to the motor 112. However, potentiometers can add an additional component to the design and waste heat and energy from efficiency loss. A preferred embodiment could use pulse width modulation (PWM) to control voltage supply to the motor 112. This control method modulates pulses of the same magnitude voltage over variable time periods to produce an "effective" level of voltage supply. For example, PWM control of a 12V power supply would control longer duration pulses to create an "average" supply of 10V, whereas PWM control of that same 12V power supply would control shorter duration pulses to create an "average" supply of 4V. These pulses are modulated by timed control of transistors which can be turned on and off by the CPU 110.

This method can be more precise and more efficient than the use of a potentiometer. Those skilled in the art will know of other ways to control and vary precise power delivery aside from using PWM. An alternate embodiment could independently control pressure and vacuum supplied to a pneumatically-sealed trocar via two independent DC pumps, as shown in FIG. 2. This embodiment involves controlling one pump 214 to provide positive pressure and flow to the pneumatically-sealed trocar 216 and a separate pump 314 to provide a balancing negative pressure and return flow away from the trocar 216. This embodiment would allow for separate, real-time, independent control over the pressure flow and return/vacuum flow which could allow for a new paradigm of granular performance control. In this embodiment, both pumps would be open to ambient and their performance would not be affected or limited by a single, closed-loop pneumatic circuit.

Whereas in the previous embodiment of FIG. 1 (and the system disclosed in U.S. Pat. No. 8,715,219) the single pump pressurizes one side of the pneumatic circuit and applies suction to the other side of the circuit to create a balanced flow on both sides, this alternate embodiment shown in FIG. 2 would allow for the system 200 to control the pressure and return flows to different flow rates. This system enables the electro-mechanical control to use an additional control lever over the performance of the pneumatically-sealed trocar 216. It is posited that small-scale adjustments (perhaps on the order of 0.1 L/min) to change the balance of the pressure flow versus the vacuum/return flow could allow for tighter control of pneumatic performance of the trocar 216.

For example, if the loop controller has a small, positive control deviation (the difference between measured performance and targeted performance in an embedded control system) then the CPU 210 could call for a 0.1 L/min increase to the pressure pump 214 or a 0.1 L/min decrease to the suction pump 314 to balance performance, whereas previously it was impossible to create an imbalance between those two flow rates. This embodiment would require the pressure pump 214 to be open to ambient for its intake, and the vacuum/suction pump 314 to be open to ambient for exhaust. It is envisioned that the open intake to the pressure pump 214 and the open exhaust from the vacuum pump 314 would be filtered through a suitable filtration device or element.

Those skilled in the art will readily appreciate that there are a number of advantages to using a DC-based control system instead of an AC-based system for the pneumatic control of a pneumatically-sealed trocar. A DC-based control system is more energy efficient than an AC-based system. An AC pump needs to be oversized in order to fully encompass the operating range of the electro-mechanical control system. The nature of AC components is that they are always fully "on", meaning that full power is required whenever the device is run.

In a DC-based system, the pump(s) need only be powered to the exact level that is required. For example, if a system has an operating range up to 100 L/min, but a use scenario only requires an output of 20 L/min, the AC-based embodiment requires the single AC pump to be outputting 100 L/min (with 80 L/min diverted away), while the DC-based embodiment could power the DC pump only to a level that outputs 20 L/min. Not only is this arrangement more energy efficient, it reduces heat and sound generated by the moving mechanical components. As a result, it may be possible to reduce or eliminate insulating components in the design.

In addition, it may allow for fewer components, as the valve/sensors to divert flow from the AC pump output are no longer required. Fewer components allow for simpler development processes and qualification testing and will result in a cost-savings both for cost of goods and development. Furthermore, the use of a DC-based control system will not be subject to the effects that power frequency has on AC motors and pumps, whereby different power grids around the world supply power at different frequencies (typically either 50 Hz or 60 Hz). When powering an AC motor or pump, the output performance is slightly altered by the frequency, whereas a DC motor or pump can produce the same behavior no matter the frequency.

Finally, whereas typical AC components like a pump are dependent on power supply (the pump might have different models for a 100/115 V grid versus a 230 V grid), a DC pump enables a single, global design as the power transformer merely needs to transform input voltage to 12 V to power the motor. This gives advantages in inventory control and economies of scale when manufacturing, which will lower the cost of goods. It can also eliminate the need for developing, qualifying, and documenting multiple versions of each device for different power grids.

While the subject disclosure has been shown and described with reference to preferred embodiments, those skilled in the art will readily appreciate that changes and/or modifications may be made thereto without departing from the scope of the subject disclosure.

What is claimed is:
1. A system for controlling the performance range of a pneumatically sealed trocar, comprising:
   a) a controller for delivering variable DC voltage to at least one DC motor;
   b) at least one DC motor operatively connected to the controller for driving at least one pump operatively connected to a pneumatically sealed trocar;
   c) at least one pump driven by the DC motor for circulating pressurized gas through the pneumatically sealed trocar; and d) at least one sensor for sensing pressure and/or flow parameters between the at least one pump and the pneumatically sealed trocar to provide at least one feedback control signal to the controller so that the controller can vary the voltage delivered to the at least one DC motor to affect the output pressure and/or flow of the at least one pump during a surgical procedure, wherein the at least one sensor includes a first sensor for sensing positive pressure and flow parameters between the at least one pump and an inlet port of the pneumatically sealed trocar to provide a first feedback control signal to the controller and a second sensor for sensing negative pressure and/or flow parameters between the at least one pump and an outlet port of the pneumatically sealed trocar to provide a second feedback control signal to the controller.

2. A system as recited in claim 1, further comprising an AC input voltage source and an AC-DC converter for supplying DC voltage to the controller.

3. A system as recited in claim 1, further comprising a pneumatically sealed trocar connected to the at least one pump for providing pneumatically sealed access to a body cavity of a patient during the surgical procedure.

4. A system as recited in claim 1, wherein the at least one DC motor includes a first DC motor for driving a positive pressure pump connected to the pneumatically sealed trocar and a second DC motor for driving a negative pressure pump connected to the pneumatically sealed trocar.

5. A system as recited in claim 4, wherein the at least one sensor includes a first sensor for sensing positive pressure and/or flow parameters between the positive pressure pump and an inlet port of the pneumatically sealed trocar to provide a first feedback control signal to the controller and a second sensor for sensing negative pressure and/or flow parameters between the negative pressure pump and the outlet port of the pneumatically sealed trocar to provide a second feedback control signal to the controller.

6. A system as recited in claim 1, wherein the at least one pump includes at least first and second pumps arranged in parallel and wherein the controller is adapted and configured to control the first and second pumps at the same or different output levels to meet system requirements.

7. A system as recited in claim 6, wherein the at least first and second pumps are driven by respective first and second DC motors.

\* \* \* \* \*